(12) United States Patent
Haritou et al.

(10) Patent No.: US 12,269,244 B2
(45) Date of Patent: Apr. 8, 2025

(54) WALL STRUCTURE MONITORING SYSTEM

(71) Applicants:Christos Haritou, New Marske (GB); Alan Fada, Washington (GB)

(72) Inventors: Christos Haritou, New Marske (GB); Alan Fada, Washington (GB)

( * ) Notice: Subject to any disclaimer, the term of this patent is extended or adjusted under 35 U.S.C. 154(b) by 300 days.

(21) Appl. No.: 17/640,439

(22) PCT Filed: Sep. 7, 2020

(86) PCT No.: PCT/GB2020/052145
§ 371 (c)(1),
(2) Date: Mar. 4, 2022

(87) PCT Pub. No.: WO2021/044174
PCT Pub. Date: Mar. 11, 2021

(65) Prior Publication Data
US 2022/0340357 A1   Oct. 27, 2022

(30) Foreign Application Priority Data

Sep. 24, 2019   (GB) .................................... 1913737

(51) Int. Cl.
| | | |
|---|---|---|
| *B32B 3/02* | (2006.01) | |
| *B32B 5/02* | (2006.01) | |
| *B32B 5/26* | (2006.01) | |
| *B32B 7/08* | (2019.01) | |
| *B32B 7/12* | (2006.01) | |
| *B65D 90/02* | (2019.01) | |
| *B65D 90/51* | (2019.01) | |
| *G01D 11/24* | (2006.01) | |

(52) U.S. Cl.
CPC ............... *B32B 3/02* (2013.01); *B32B 5/022* (2013.01); *B32B 5/263* (2021.05); *B32B 7/08* (2013.01); *B32B 7/12* (2013.01); *B65D 90/02* (2013.01); *B65D 90/51* (2019.02); *G01D 11/245* (2013.01); *B32B 2255/02* (2013.01); *B32B 2255/26* (2013.01); *B32B 2262/101* (2013.01); *B32B 2307/536* (2013.01); *B32B 2307/718* (2013.01); *B32B 2307/7265* (2013.01); *B32B 2307/732* (2013.01); *B32B 2405/00* (2013.01); *B32B 2439/00* (2013.01); *B65D 2590/023* (2013.01)

(58) Field of Classification Search
CPC ............ B32B 2607/02; B32B 2439/40; B32B 2255/26; B32B 2439/00; B32B 5/06; B32B 3/06; B32B 3/04; B32B 2307/714; B65D 2590/023; B65D 90/02; B65D 90/22; B65D 90/51; B65D 90/50; G01D 11/245; G01N 17/006; G01N 2033/0096; G01N 33/208
See application file for complete search history.

(56) References Cited

U.S. PATENT DOCUMENTS

| | | | |
|---|---|---|---|
| 2005/0193839 A1* | 9/2005 | Gronvall | ............... G01D 11/245 73/866.5 |
| 2007/0144272 A1* | 6/2007 | Yu | .......................... G01N 17/02 73/862.046 |

FOREIGN PATENT DOCUMENTS

CN    102873949 A  *  1/2013

* cited by examiner

*Primary Examiner* — John Fitzgerald
*Assistant Examiner* — Truong D Phan
(74) *Attorney, Agent, or Firm* — Kinney & Lange, P.A.

(57) ABSTRACT

A wall having a fluid impervious coating thereon and further having a monitoring arrangement which provides for monitoring the condition of the wall. The monitoring arrangement mounted on a surface of the wall.

14 Claims, 6 Drawing Sheets

WALL STRUCTURE MONITORING SYSTEM

FIELD OF THE INVENTION

The present invention relates to wall structures, of a tank for example, and in particular to the monitoring thereof. Wall structures may comprise one or two skins. Where two skins are provided the inner and outer skins may be separated by an interstitial space.

BACKGROUND OF THE INVENTION

Structures, such as tanks are commonly used for storing fluids. Environmental damage may occur if a fluid storage tank leaks. Obviously the nature and extent of damage caused by leakage from a tank will depend on the nature of the fluid in the tank and the amount of leakage. Where tanks are above-ground, the wall areas can be monitored by visual inspection, however floor plates must be inspected when the tank is empty. In some countries there is a legal requirement for owners of storage tanks to risk manage their cargo storage as per EEMUR 159 and API 652 and 653 standards. The ability to monitor the integrity of an above-ground tank would save labour and provide for monitoring of those parts of the tank that are difficult to inspect, reducing expenditure whilst at the same time being in complete control of pollution management. In many circumstances fluid storage tanks are located underground. Underground fuel storage tanks are used at filling stations for the storage of petroleum products. Leakage of petroleum products from an underground storage tank might go unnoticed for many months, during which time water courses may be polluted, and soil may be contaminated. Furthermore, people and buildings in the vicinity may be endangered by the presence of highly flammable fuels in the ground.

Historically, underground fuel storage tanks were fashioned from a single skin of mild steel. Corrosion of such tanks was not a problem whilst petrol fuel contained lead, the lead acting as a corrosion inhibitor. However, in most countries lead is no longer present in petrol fuel. Lead free petrol fuel is corrosive of steel, and there have been a number of incidences of such tanks leaking fuel into the ground with consequent damaging effects. Where bio-fuels are used sulphate reducing bacteria can also lead to corrosion of storage tanks. There is therefore a move to line underground fuel storage tanks with linings not susceptible to corrosion by the fuel destined to be stored in the tank.

If a double skinned tank contains an air gap between the outer tank wall and the interior lining, leakage from the tank can be monitored by various leak monitoring devices. One such leak monitoring device monitors a vacuum in the air gap. A change in pressure indicates an integrity failure in the inner lining or outer hull.

The replacement of an underground or above ground tank is a time consuming and expensive process, since in the case of a filling station, the cost of physically removing the tank from the ground is itself high, but more importantly whilst the tank is being replaced the fuel station must be closed, resulting in loss of revenue for the period of closure, and possible long-term loss of business due to customers going to other filling stations during the period of closure. When considering the cost of refurbishing an above ground tank, during the refurbishment time the tank cannot be used, and depending on the nature of the fluids stored in any adjacent tanks, it might be necessary to empty those tanks and keep them empty during the refurbishment.

Re-lining existing underground and or above ground tanks provides at least three benefits. First, the lining is typically selected so as not to be corrodible by the fuel. Second, if there is an interstitial space this space can be monitored to establish whether there is any leakage of fuel from the tank, and third, lining a tank can be accomplished more quickly than replacement of a tank.

An apparatus and method for lining a tank so as to provide a monitor able interstitial space is described in GB2444486. The apparatus uses sheet material having adhesive applied to both sides to attach itself and other components of the lining to the wall of the tank. The apparatus and method described in this invention have been found to be particularly effective in the lining of both underground and above-ground fuel storage tanks.

It has also been recognised that above-ground tanks are susceptible to corrosion, in particular external corrosion, especially in the bottom walls thereof. An above-ground tank may comprise a bottom wall formed of a bottom plate and an annular ring. Standards may require a specific inspection regime be put in place to monitor a part of a tank, for example the annular ring thickness and/or the bottom plate thickness.

Ultrasound non-destructive testing is used for assessing the condition of tank walls both when empty and the tank is being used. However, when the tank is in use only limited data can be obtained through ultrasound testing. For example, wall thickness may be measured from time to time when the tank is partially empty (the measurement being tank above the fluid level). If the wall thickness is falling this can be interpreted as indicating that the tank is corroding. It can be assumed that the bottom wall is also corroding. Action may then be taken to empty the tank and inspect the bottom wall directly.

Vacuum monitoring systems are capable of indicating a failure in a wall of a double skinned tank. It would be desirable to monitor the condition of the wall of a structure so that corrosion of the wall may be detected before the wall actually fails.

Whilst double skinned structures are being adopted more widely, many single skinned structures, such as tanks and pipes continue in use and new single skinned tanks continue to be deployed.

It would therefore be desirable to provide a monitoring system that is useful in monitoring the integrity of a single skinned structure.

SUMMARY OF THE INVENTION

According to a first aspect of the invention there is provided a wall having a fluid impervious coating thereon and further comprising a monitoring arrangement which provides for monitoring the condition of the wall, the monitoring arrangement mounted on a surface of the wall.

The coating may have a nominal thickness of at least 500 micron or at least 1270 micron. The coating may be any coating with the capacity to fulfil the resistance of stored cargo to protect the tank steel, such as epoxy resin coating and/or solvent free.

The monitoring arrangement may comprise at least one housing attached to the wall and extending to the same side thereof as the fluid impervious coating, the housing having a removable and closure member that is fluid tight when closed, the housing providing access to a part of the structural wall that is not coated by the fluid impervious coating.

The at least one housing may include a plate for attachment to the structural wall and a chamber that is attached to the plate, the closure member located in an opening in the chamber.

The plate may have an opening therein through which access to the structural wall may be gained, and wherein the chamber has a corresponding opening, the two openings being aligned when the chamber is mounted on the plate.

The wall may further comprise monitoring means configured for monitoring the condition of the structural wall.

The monitoring means may further comprise at least one sensor.

The at least one sensor may be connected to an external data receiving by a wired or wireless connection.

The at least one sensor may be situated between the wall and the fluid impervious coating.

Advantageously, the monitoring means is mounted in the housing or within a protective member.

According to a second aspect of the invention there is provided a method of fabricating a wall as claimed in any preceding claim, comprising the steps of:
i. cleaning an inner surface of a wall;
ii. mounting the monitoring arrangement on the inner surface of the wall; and wherein the inner surface of the wall and at least a part of the monitoring arrangement have a fluid impervious coating applied thereto.

The method may comprise the step of mounting a plurality of mentoring arrangements on the inner surface of the wall.

According to a third aspect of the invention there is provided a structure comprising at least one wall, wherein at least one wall of the structure is a wall according to the first aspect of the invention.

The structure may be one of: a tank, a pipe, a turbine support structure, a water borne platform structure or part thereof, a building support structure, and a bridge support structure.

Advantageously, at least one of the walls of the structure is provided with a plurality of monitoring arrangements.

Whilst the invention has been described in relation to a singled skinned structure where the wall is coated with a fluid impervious coating, a second skin separated from the coated wall by an interstitial space may be arranged to one side of the wall.

BRIEF DESCRIPTION OF THE DRAWINGS

In the drawings, which illustrate preferred embodiments of the invention, and which are by way of example:

FIG. 2b is an exploded view of assembled components illustrated in FIG. 11a;

DETAILED DESCRIPTION OF THE PREFERRED EMBODIMENTS

Figure 1:
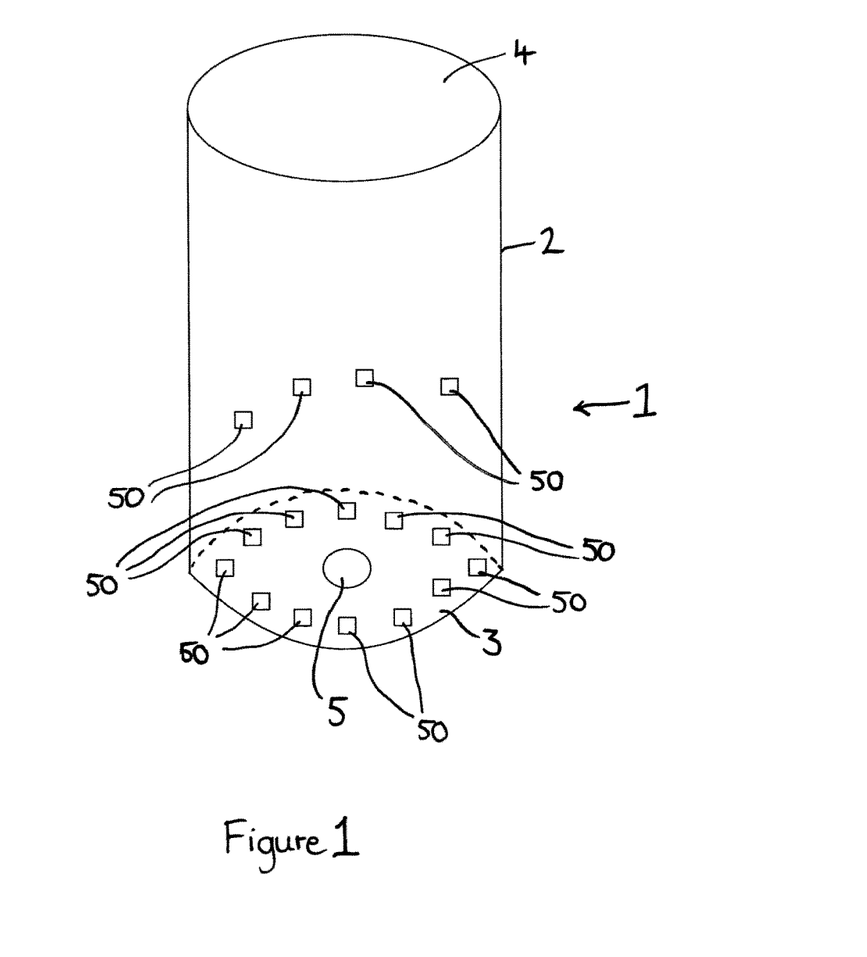
FIG. 1 is schematic representation of an above ground tank.

Referring now to FIG. 1, which illustrates an above ground tank 1 comprising a side wall 2 a bottom wall 3 and a top wall 4. The bottom wall 3 and the side wall 2 are provided with sensors 50 (which are described in greater detail with reference to FIGS. 5 and 6 below). The walls of the tank in the illustrated example are single skinned, that is there is one wall rather that two walls separated by an interstitial space. The walls may be formed of metal such as steel and may be coated with a corrosion resistant material. The thickness of corrosion resistant coating will depend on the condition of the walls prior to application of the corrosion resistant coating. For example, where the tank is new and the metal of the walls is substantially free of corrosion a coating that is relatively thin may be used, whereas where the tank is being refurbished following significant corrosion of the walls a comparatively thicker coating will be required as described in greater detail below. The bottom wall 3 of the tank 1 is provided with a sump 5 which provides for emptying of the tank 1.

Prior to application of a corrosion resistant coating the surface of wall 1 is prepared by cleaning, typically by shot blasting and then a layer of solvent free (or solvented) resin is applied to a thickness of between 500 micron and 1500 micron. Where there has been significant surface corrosion the surface can be pitted post cleaning. Where such surface pitting exists the nominal thickness of the solvent free resin coating will typical be 1270 micron or greater and preferably in the range 1270-1500 micron. Where there is little or no pitting the solvent free resin coating is applied to a nominal thickness of 500 micron to 1000 micron. Nominal thickness means an average of the thicknesses of the coating measured at a number of, for example 100, points. The solvent free resin is usually applied by spraying using equipment that is widely available and known in the art. In the illustrated example, the solvent free resin is a two component polycyclamine epoxy and includes glass flake and fibre reinforcement. The polycyclamine epoxy is a novolac epoxy resin. One solvent free resin having these properties is Enviroline (registered trade mark) 376F-60 (SPL) available from Akzo Nobel.

The solvent free resin coat is allowed to cure for 24 hours. The surface provided by the cured resin is in itself impervious to fluids such as water, fuel, oil etc. If the solvent free coating is applied to a sufficient thickness, that is greater than 1270 micron, the cured solvent free epoxy resin coating can bridge holes in the metal of wall 1 of up to 50 mm diameter.

If after cleaning, pits in the wall are too deep to be covered adequately by the sprayed on solvent free epoxy resin, any such pits can be filled with a two part epoxy filler that is compatible with the solvent free epoxy resin. Once pits are filled the solvent free epoxy coating may be applied to the cleaned metal surface and any filler applied thereto. Suitable fillers include Hempel ProFiller 35370 from Hempel A/S and AWLFAIR LW D8200/D7200 from Akzo Nobel.

Figure 2A:
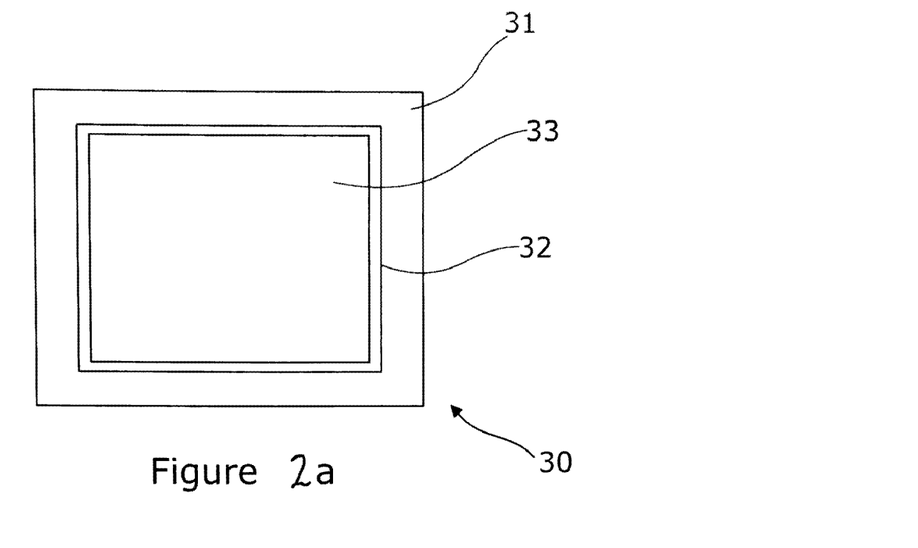
FIG. 2a is a plan view of an inspection assembly comprising a plate for attachment to a tank wall and an inspection port box connected thereto.

Above-ground structures (tanks in particular) are susceptible to external corrosion, especially in the bottom wall thereof, which is often inaccessible. FIG. 2a illustrates an inspection assembly 30 comprising a plate 31 for attachment to a tank wall and an inspection port box 32. The plate 31 includes a hole 31a. The inspection port box 32 also includes a hole 32a which aligns with the hole 31a when the inspection port box 32 is mounted on the plate 31. The inspection port box 32 is welded to the plate 31. The inspection port box 32 is provided with a lid 33 that is removable from the box 32. A seal, not shown, is provided between the lid 33 and the box 32.

Figure 2B:
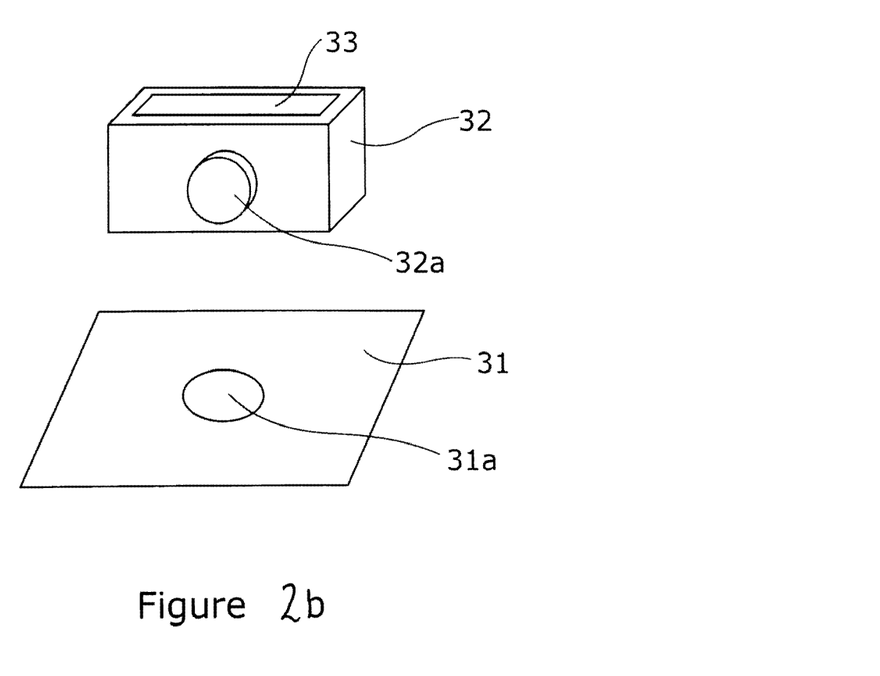

The inspection assembly 30 illustrated in FIGS. 2a and 2b is relatively small, the port plate being approximately 115 mm×115 mm, with the inspection port box 32 being approximately 76 mm×76 mm. The holes 31a, 32a in the example are approximately 50 mm in diameter. The sizes of the components of the inspection assembly are given by way of example only.

Figure 3:
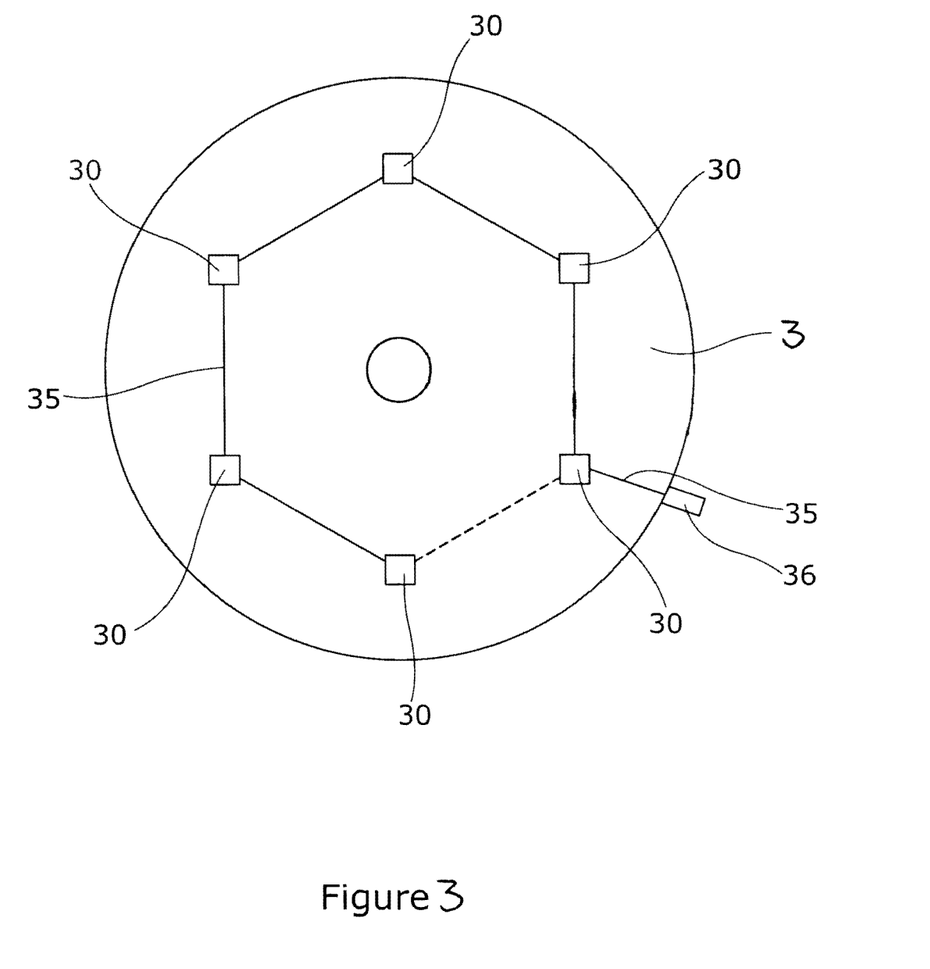
FIG. 3 illustrates a tank bottom wall provided with a plurality of inspection assemblies of the type illustrated in FIGS. 11a and 11b with provision for remote mon toeing.

FIG. 3 illustrates the inside surface of the bottom wall 3 of an above-ground tank, the bottom wall 3. In the illustrated example, six inspection assemblies 30 are attached to the bottom wall 3 at spaced apart locations. The surfaces of the plate 31, the walls of the inspection box 32 and the lid 33 that face into the tank 1 are coated with the same or a similar coating to the inner surfaces of the walls 2-4 of the tank 1.

Figure 4:
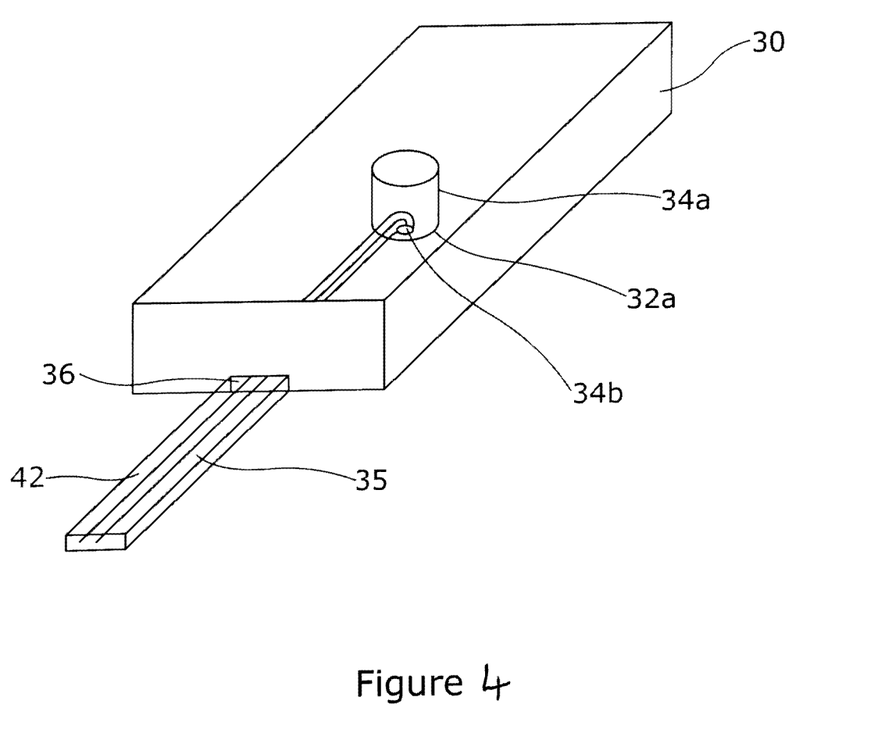
FIG. 4 is a schematic representation of the inspection box illustrated in FIGS. 11a and 11b provided with instrumentation.

Referring now to FIGS. 3 and 4, the inspection boxes 32 are provided with sensor ports 34a each equipped with a sensor 34b for monitoring the condition of the bottom wall 3. The sensor ports 34a sit in the hole 32a in the inspection port box 32. The sensor ports 34a each comprise a block of metal such as mild steel in which the sensor 34b is mounted. The sensors 34b may be ultrasonic sensors. Signals from the sensors may be conveyed to an external data receiving system by wires 35 or by means of wireless communication. In the wired arrangement illustrated in FIGS. 3 and 4 the inspection boxes 32 are provided with ports 36 through which the wires 35 pass. The ports 36 are sealed against ingress of fluid when the wires have been passed through the ports. It is preferred that the wires 35 are encapsulated and therefore separated from the contents of the tank. In the illustrated example, trunking 42 is provided. This trunking may sit on top of the fluid impervious coating covering the bottom wall 3. The trunking may be attached to the fluid impervious coating of the bottom wall 3 by means of a suitable adhesive. The trunking may then be coated with the same or a similar fluid impervious coating to that applied to the liner surface of the wall 3. The wires 35 exit the tank via a pipe penetration apparatus which allows the wires 35 to be accessed whilst preventing egress of fluid from the tank.

The inspection boxes 32 illustrated in FIGS. 2 to 4 provide for manual inspection of the bottom wall 3. Inspection is carried out by draining the content of a tank, for example via sump 5, entering the tank and removing the lid 33. The bottom wall 3 may be inspected visually through the holes 31a, 32a or by using non destructive testing equipment that is brought to the tank. There the inspection box is equipped with sensor ports 34a and sensor 34b, the wall 3 may be inspected manually by removing the sensors port 34a from the hole 32a of the inspection box 32.

By providing for both manual and remote inspection it is possible that manual inspection cycles may be lengthened, whilst providing for corrosion to be detected earlier than high occur with manual inspection only.

Figure 5:
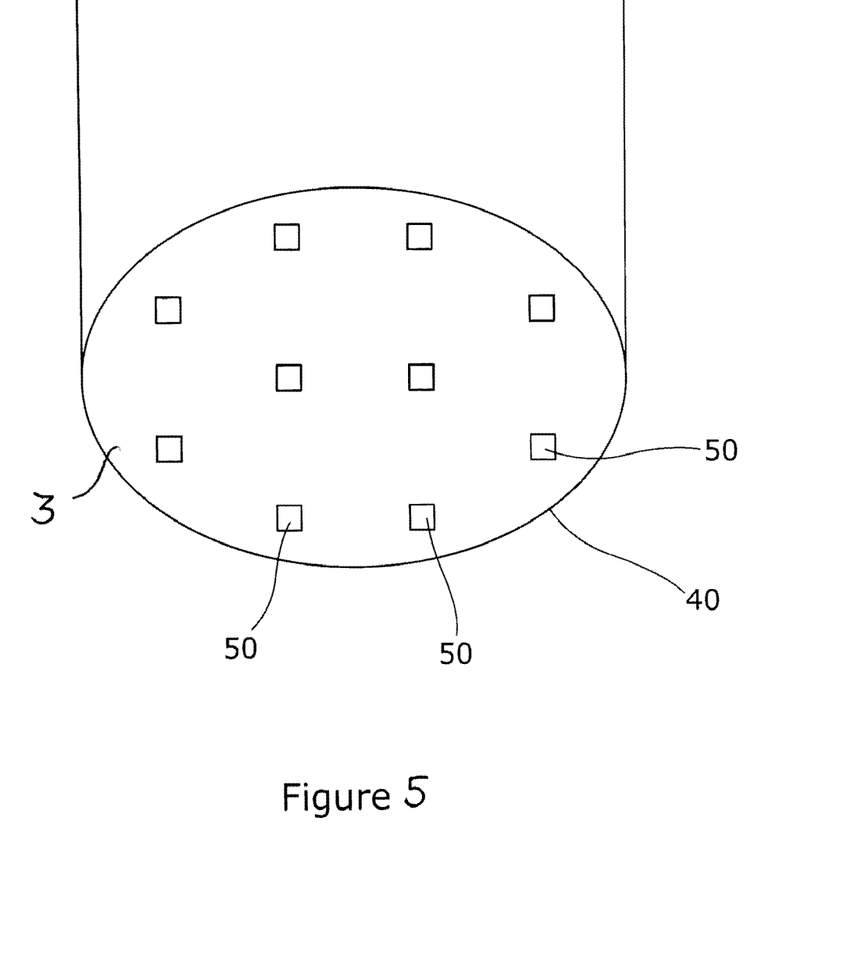
FIG. 5 illustrates a tank bottom wall provided with an alternative type of monitoring arrangement.

FIG. 5 illustrates a bottom wall 3 of the above-ground tank that is instrumented with sensors 50, typically ultrasound sensors, which are encapsulated within the fluid impervious coating described above. In this arrangement, manual inspection of the bottom wall 3 is not possible. The ultrasound sensors 50 are equipped are wireless enabled so that data can be transmitted to an external data receiver. Alternatively, the sensor 50 could be connected by wires to an external data receiver. Where wired connections are used, trunking similar to described with reference to FIG. 4 may be deployed. The ultrasound sensors 50 are shown distributed around the bottom wall 3. The sensors 50 may be distributed around the tank so that the condition of specific components of the tank. For example, the bottom wall may comprise a bottom plate and an annular ring. One or both of these components may be provided with a number of sensors. Advantageously, the sensors are identifiable by the external data receiving means. For example, if the sensors are wirelessly enabled each may have its now identification code. Where the sensors are wired, those wires may be connected such that the location of respective sensors may be identified.

Figure 6:
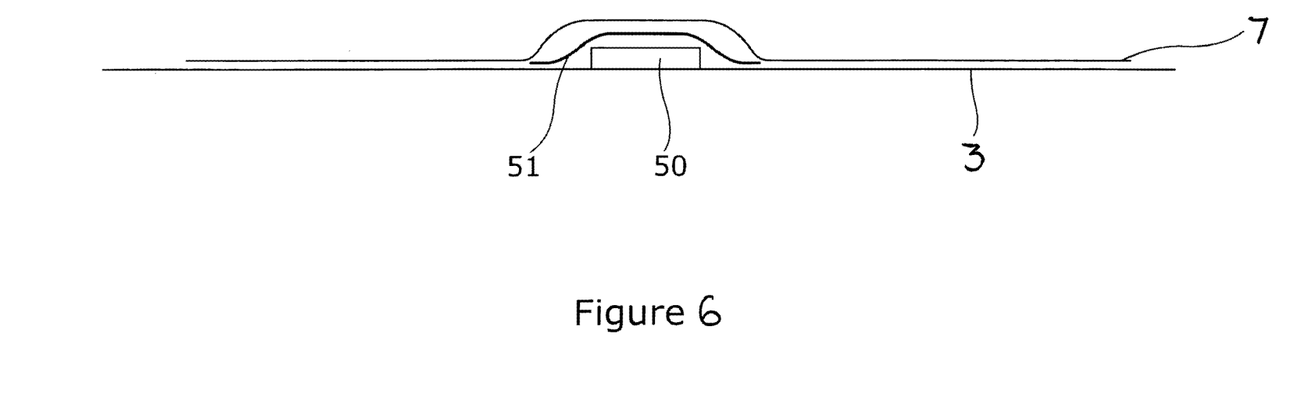
FIG. 6 is a schematic cross-sectional view of the mounting arrangement illustrated in FIG. 5.

FIG. 6 illustrates one of the sensors 50 situated between the bottom wall 3 and a layer of fluid impervious coating 7 as described generally with reference to FIG. 1 for example. The sensor 50 is attached by means of a suitable adhesive to the surface of the structural wall 3 after its surface has been cleaned, typically by blasting thereof. A protective cap 51 is located over the sensor 50. The cap 51 is also attached to the surface of the structural wall 3 by adhesive. The function of the cap 51 is to protect the sensor 50 from inadvertent damage, for example if the sensor 50 were to be walked on. The cap may be formed from pressed steel or a plastic. Typically, it is only the area of the wall 3 immediately beneath the sensor 50 that is not coated with the fluid impervious coating. Where the fluid impervious coating is taken up to the edge of the sensor 50 the cap 51 is attached to that fluid impervious coating, typically by adhesive, and a further layer of fluid impervious coating is applied over the cap 51 and the area of the coated wall 3 immediately around the cap 51. Of course, the cap 51 may be attached to the surface of the wall 3 before the fluid impervious coating is applied thereto. In this case, the fluid impervious coating is applied over the surface of the wall 3 and the cap 51.

The invention has been described in relation to a tank. However, other types of structure may benefit from the invention. For example, wind turbine towers, oil rig legs, large diameter pipes, etc. In relation to tanks, it is not only fuel tanks that may benefit from the monitoring arrangements described herein. Many liquids have corrosive properties and hence preventing contact between such liquids and the structural wall may be useful. Also, liquids may not be corrosive to a structure, but they may be harmful to the environment if they escape, and walls of a tank may be subject to external corrosion. Hence, providing a means by which the condition of the wall of a tank may be monitored is beneficial.

The invention claimed is:

1. A wall having a fluid impervious coating on an inner surface thereof and further comprising a monitoring arrangement which provides for monitoring the condition of the wall, the monitoring arrangement mounted on the inner surface of the wall, the inner surface of the wall and at least a part of the monitoring arrangement having the fluid impervious coating applied thereto, the monitoring arrangement including one of: a housing attached to and enclosing an enclosed region of the inner surface of the wall, the housing having an outer surface and extending to the same side thereof as the fluid impervious coating, the fluid impervious coating being applied to a part of the outer surface of the housing, the housing having a removable closure member that is fluid tight when closed, the housing providing access to the enclosed region of the inner surface of the wall that is not coated by the fluid impervious coating, wherein a space is formed between the inner surface of the wall in the enclosed region and an underside of the removable closure member; and a protective member attached to the inner surface of the wall, the protective member enclosing a region of the inner surface, wherein the protective member is situated between the inner surface of the wall and the fluid impervious coating and the enclosed region of the inner surface of the wall is not coated by the fluid impervious coating and wherein a space is formed between the inner surface in the enclosed region and an underside of the protective member.

2. A wall according to claim 1, wherein the coating has a nominal thickness of one of: at least 500 micron and at least 1270 micron.

3. A wall according to claim 1, wherein the coating is a resin coating.

4. A wall according to claim 3, wherein the resin is one of: solvent free and solvented.

5. A wall according to claim 3, wherein the resin is an epoxy resin.

6. A wall according to claim 1, wherein the housing includes a plate for attachment to the wall and the enclosed region is formed between the plate and the closure member.

7. A wall according to claim 6, wherein the plate has an opening therein through which access to the wall may be gained, the opening in the plate communicating into the enclosed region of the housing.

8. A wall according to claim 1, further comprising: monitoring means configured for monitoring the condition of the wall.

9. A wall according to claim 8, wherein the monitoring means comprises at least one sensor.

10. A wall according to claim 9, wherein the at least one sensor is connected to an external data receiving by one of a wired and wireless connection.

11. A wall according to claim 9, wherein the at least one sensor is mounted in one of: the housing and the protective member.

12. A structure comprising at least one wall, wherein the at least one wall of the structure is a wall having a fluid impervious coating thereon and further comprising a monitoring arrangement which provides for monitoring the condition of the wall, the monitoring arrangement mounted on a surface of the wall, the monitoring arrangement including one of: a housing, attached to and enclosing a region of the inner surface of the wall, the housing having an outer surface and extending to the same side thereof as the fluid impervious coating, the fluid impervious coating being applied to a part of the outer surface of the housing, the housing having a removable closure member that is fluid tight when closed, the housing providing access to the enclosed region of the inner surface of the wall that is not coated by the fluid impervious coating, wherein a space is formed between the inner surface of the wall in the enclosed region and an underside of the removable closure member; and a protective member attached to the inner surface of the wall, the protective member enclosing a region of the inner surface, wherein the protective member is situated between the inner surface of the wall and the fluid impervious coating and the enclosed region of the inner surface of the wall is not coated by the fluid impervious coating and wherein a space is formed between the inner surface in the enclosed region and an underside of the protective member.

13. A structure according to claim 12, wherein the structure is one of: a tank, a pipe, a turbine support structure, a water borne platform structure, a water bourne platform structure component part, a building support structure, and a bridge support structure.

14. A structure according to claim 12, wherein the at least one wall of the structure is provided with a plurality of monitoring arrangements.

\* \* \* \* \*